United States Patent
Zhong (12)

(10) Patent No.: US 6,231,600 B1
(45) Date of Patent: May 15, 2001

(54) STENTS WITH HYBRID COATING FOR MEDICAL DEVICES

(75) Inventor: Sheng-ping Zhong, Northborough, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/320,340

(22) Filed: May 26, 1999

Related U.S. Application Data

(60) Continuation-in-part of application No. 08/929,948, filed on Sep. 15, 1997, now Pat. No. 6,048,620, which is a division of application No. 08/392,141, filed on Feb. 22, 1995, now Pat. No. 5,702,754.

(51) Int. Cl.$^7$ ............... A61I 2/06; A61L 27/00; A61L 33/00

(52) U.S. Cl. ............... 623/1.42; 623/1.43; 623/1.46; 427/2.24; 427/402; 428/423.1; 428/424.4

(58) Field of Search ............... 623/1.42, 1.43, 623/1.46; 427/2.24, 402; 428/423.1, 424.4

(56) References Cited

U.S. PATENT DOCUMENTS

| | | |
|---|---|---|
| 3,663,288 | 5/1972 | Miller ........................... 117/7 |
| 3,779,792 | 12/1973 | Stoy et al. ..................... 117/72 |
| 4,047,957 | 9/1977 | De Winter et al. ............. 96/67 |
| 4,100,309 | 7/1978 | Micklus et al. ................ 427/2 |
| 4,119,094 | 10/1978 | Micklus et al. ............ 128/132 R |
| 4,263,188 | 4/1981 | Hampton et al. ......... 260/29.2 TN |
| 4,306,998 | 12/1981 | Wenzel et al. ................ 260/13 |
| 4,373,009 | 2/1983 | Winn ........................... 428/424.2 |
| 4,387,024 | 6/1983 | Kurihara et al. ............ 210/490 |
| 4,391,797 | 7/1983 | Folkman et al. ............. 424/19 |
| 4,459,317 | 7/1984 | Lambert ........................ 427/2 |
| 4,487,808 | 12/1984 | Lambert ....................... 428/423.1 |
| 4,536,179 | 8/1985 | Anderson et al. ............ 604/266 |
| 4,548,844 | 10/1985 | Podell et al. ................. 428/35 |
| 4,642,267 | 2/1987 | Creasy et al. ................ 428/413 |
| 4,666,437 | 5/1987 | Lambert ........................ 604/265 |
| 4,675,361 | 6/1987 | Ward, Jr. ....................... 525/92 |
| 4,692,352 | 9/1987 | Huddleston .................. 427/208.4 |
| 4,705,709 | 11/1987 | Vailancourt .................. 428/36 |
| 4,721,117 | 1/1988 | Mar et al. ..................... 128/772 |
| 4,748,986 | 6/1988 | Morrison et al. ............. 128/772 |
| 4,768,507 | 9/1988 | Fischell et al. ............... 128/303 R |
| 4,770,664 | 9/1988 | Gogolewski ................. 623/66 |
| 4,833,014 | 5/1989 | Linder et al. ................ 428/308.4 |
| 4,841,976 | 6/1989 | Packard et al. .............. 128/657 |
| 4,867,173 | 9/1989 | Leoni ........................... 128/772 |
| 4,876,126 | 10/1989 | Takemura et al. ........... 428/35.7 |
| 4,884,579 | 12/1989 | Engelson ...................... 128/772 |
| 4,923,464 | 5/1990 | DiPisa, Jr. ..................... 606/195 |
| 4,925,698 | 5/1990 | Klausner et al. ............ 427/2 |
| 4,943,460 | 7/1990 | Markle et al. ................ 428/36.9 |
| 4,959,074 | 9/1990 | Halpern et al. .............. 623/66 |
| 4,964,409 | 10/1990 | Tremulis ...................... 128/657 |
| 4,969,890 | 11/1990 | Sugita et al. ................. 606/192 |

(List continued on next page.)

FOREIGN PATENT DOCUMENTS

| | | |
|---|---|---|
| 556 350 A1 | 10/1983 | (AU) . |
| 556 351 A1 | 10/1986 | (AU) . |
| 0 093 094 A1 | 11/1983 | (EP) . |
| 0 106 004 A1 | 4/1984 | (EP) . |

(List continued on next page.)

OTHER PUBLICATIONS

Bartoli et al., "In Vitro and In Vivo Antitumoral Activity of Free, and Encapsulated Taxol", *J. Microencapsulation*, vol. 7, No. 2 (1990) pp. 191–197.

Bruck, Stephen D., "Interactions of Synthetic and natural surfaces with blood in the Physiological Environment," *J. Biomed. Mater. Res. Symposium*, No. 8 (1997) pp. 1–21.

Cox, David A., M.D. et al., "Effect of Local Delivery of Heparin and Methotrexate on Neointimal Proliferation in Stented Porcine Coronary Arteries", *Coronary Artery Disease*, vol. 3, No. 3, Mar. 1992, pp. 237–248.

Cox, D. A. et al., "Local Delivery of Heparin and Methotrexate Fails to Inhibit In Vivo Smooth Muscle Cell Proliferation", *Supplement to Circulation Abstracts From the 64$^{th}$ Scientific Sessions*, vol. 84, No. 4, Abstract No. 0284, 1991, p. II–71.

Dev, V. et al. "Kinetics of Drug Delivery to the Arterial Wall Via Polyurethane Coated Removable Nitinol Stent–Comparative Study of 2 Drugs", *Circulation Abstracts From the 66$^{th}$ Scientific Sessions*, vol. 88, No. 4, Part 2, Abstract No. 1657 (1993) p. I–3.

Esquivel, Carlos O., M.D. et al., "Reduced Thrombogenic Characteristics of Expanded Polytetrafluoroethylene and Polyurethane Arterial Grafts After Heparin Bonding", *Surgery*, Jan. 1984, pp. 102–107.

(List continued on next page.)

*Primary Examiner*—David J. Isabella
*Assistant Examiner*—Choon P. Koh
(74) *Attorney, Agent, or Firm*—Crompton, Seager & Tufte, LLC

(57) ABSTRACT

A device such as a stent is provided with a hybrid coating including a time released, restenosis inhibiting coating and a non-thrombogenic coating to prevent clotting on the device. One first coat or layer includes a polymer, a crosslinking agent, and pacitaxel, analogues, or derivatives thereof. The first coat preferably includes a polymer having Taxol admixed therein so as to be releasable over time. The first coat preferably includes a polyfunctional aziridine as the crosslinking agent. The second coat preferably includes heparin to inhibit clot formation on the device. The crosslinking agent can covalently bond to both the first coat polymer and the second coat heparin. A stent can be provided with a first coat including an aqueous dispersion or emulsion of a polymer and an excess of crosslinking agent. The first coating can be dried, leaving a water insoluble polymer coating. A second aqueous coating including a solution or dispersion of heparin can be applied over the first coating, the heparin becoming covalently bound to the crosslinking agent on the first coating surface. The resulting stent can inhibit restenosis while preventing blood clot formation on the stent.

16 Claims, No Drawings

U.S. PATENT DOCUMENTS

| | | | |
|---|---|---|---|
| 4,980,231 | 12/1990 | Baker et al. | 428/36.9 |
| 4,994,071 | 2/1991 | MacGregor | 606/194 |
| 5,002,582 | 3/1991 | Guire et al. | 623/66 |
| 5,007,928 | 4/1991 | Okamura et al. | 623/6 |
| 5,008,363 | 4/1991 | Mallon et al. | 528/49 |
| 5,019,096 | 5/1991 | Fox, Jr. et al. | 623/1 |
| 5,026,607 | 6/1991 | Kiezulas | 428/423.7 |
| 5,037,656 | 8/1991 | Pitt et al. | 424/443 |
| 5,037,677 | 8/1991 | Halpern et al. | 427/338 |
| 5,040,543 | 8/1991 | Badera et al. | 128/772 |
| 5,049,403 | 9/1991 | Larm et al. | 427/2 |
| 5,057,371 | 10/1991 | Canty et al. | 428/411.1 |
| 5,066,705 | 11/1991 | Wickert | 524/457 |
| 5,067,489 | 11/1991 | Lind | 128/772 |
| 5,069,217 | 12/1991 | Fleischhacker, Jr. | 128/657 |
| 5,069,226 | 12/1991 | Yamauchi et al. | 128/772 |
| 5,079,093 | 1/1992 | Akashi et al. | 427/411.1 |
| 5,080,683 | 1/1992 | Sulc et al. | 623/66 |
| 5,080,924 | 1/1992 | Kamel et al. | 427/2 |
| 5,084,315 | 1/1992 | Karimi et al. | 428/36.6 |
| 5,091,205 | 2/1992 | Fan | 427/2 |
| 5,092,885 | 3/1992 | Yamada et al. | 623/11 |
| 5,102,401 | 4/1992 | Lambert et al. | 604/264 |
| 5,102,402 | 4/1992 | Dror et al. | 604/265 |
| 5,102,417 | 4/1992 | Palmaz | 606/195 |
| 5,105,010 | 4/1992 | Sundararaman et al. | 564/252 |
| 5,107,852 | 4/1992 | Davidson et al. | 128/772 |
| 5,128,170 | 7/1992 | Matsuda et al. | 427/2 |
| 5,129,890 | 7/1992 | Bates et al. | 604/281 |
| 5,160,790 | 11/1992 | Elton | 428/412 |
| 5,211,183 | 5/1993 | Wilson | 128/772 |
| 5,213,111 | 5/1993 | Cook et al. | 128/772 |
| 5,217,026 | 6/1993 | Stoy et al. | 128/772 |
| 5,222,971 | 6/1993 | Willard et al. | 606/158 |
| 5,240,994 | 8/1993 | Brink et al. | 525/54.2 |
| 5,241,970 | 9/1993 | Johlin, Jr. et al. | 128/772 |
| 5,243,996 | 9/1993 | Hall | 128/772 |
| 5,250,613 | 10/1993 | Bergstrom et al. | 525/54.1 |
| 5,266,359 | 11/1993 | Spielvogel | 427/388.4 |
| 5,272,012 * | 12/1993 | Opolski | 428/423.1 |
| 5,275,173 | 1/1994 | Samson et al. | 128/772 |
| 5,282,823 | 2/1994 | Schwartz et al. | 606/198 |
| 5,290,585 | 3/1994 | Elton | 427/2 |
| 5,304,121 | 4/1994 | Sahatjian | 604/53 |
| 5,304,140 | 4/1994 | Kugo et al. | 604/281 |
| 5,324,261 | 6/1994 | Amundson et al. | 604/96 |
| 5,370,614 | 12/1994 | Amundson et al. | 604/96 |
| 5,380,299 | 1/1995 | Fearnot et al. | 604/265 |
| 5,383,928 | 1/1995 | Scott et al. | 623/1 |
| 5,419,760 | 5/1995 | Narciso, Jr. | 604/8 |
| 5,423,885 | 6/1995 | Williams | 623/1 |
| 5,443,458 | 8/1995 | Eury | 604/891.1 |
| 5,443,496 | 8/1995 | Schwartz et al. | 623/1 |
| 5,447,724 | 9/1995 | Helmus et al. | 424/426 |
| 5,449,372 | 9/1995 | Schmaltz et al. | 606/198 |
| 5,449,382 | 9/1995 | Dayton | 623/1 |
| 5,464,650 | 11/1995 | Berg et al. | 427/2.3 |
| 5,512,055 | 4/1996 | Domb et al. | 604/265 |
| 5,514,154 | 5/1996 | Lau et al. | 606/195 |
| 5,527,337 | 6/1996 | Stack et al. | 606/198 |
| 5,545,208 | 8/1996 | Wolff et al. | 623/1 |
| 5,562,922 | 10/1996 | Lambert | 424/486 |
| 5,569,463 | 10/1996 | Helmus et al. | 424/426 |
| 5,576,072 | 11/1996 | Hostettler et al. | 427/532 |
| 5,578,075 | 11/1996 | Dayton | 623/1 |
| 5,591,227 | 1/1997 | Dinh et al. | 623/1 |
| 5,605,696 | 2/1997 | Eury et al. | 424/423 |
| 5,609,629 | 3/1997 | Fearnot et al. | 623/1 |
| 5,616,608 | 4/1997 | Kinsella et al. | 514/449 |
| 5,620,738 | 4/1997 | Fan et al. | 427/2.3 |
| 5,624,411 | 4/1997 | Tuch | 604/265 |
| 5,626,862 | 5/1997 | Brem et al. | 424/426 |
| 5,637,113 | 6/1997 | Tartaglia et al. | 623/1 |
| 5,651,986 | 7/1997 | Brem et al. | 424/484 |
| 5,670,507 * | 9/1997 | Rice et al. | 514/283 |
| 5,674,192 | 10/1997 | Sahatjian et al. | 604/28 |
| 5,674,241 | 10/1997 | Bley et al. | 606/198 |
| 5,674,242 | 10/1997 | Phan et al. | 606/198 |
| 5,679,400 | 10/1997 | Tuch | 427/2.14 |
| 5,697,967 | 12/1997 | Dinh et al. | 623/1 |
| 5,700,286 | 12/1997 | Tartaglia et al. | 623/1 |
| 5,702,754 | 12/1997 | Zhong | 427/2.12 |
| 5,709,874 | 1/1998 | Hanson et al. | 424/423 |
| 5,712,326 | 1/1998 | Jones et al. | 523/105 |
| 5,716,981 | 2/1998 | Hunter et al. | 514/449 |
| 5,733,925 | 3/1998 | Kunz et al. | 514/449 |
| 5,739,237 | 4/1998 | Russell et al. | 526/277 |
| 5,755,769 | 5/1998 | Richard et al. | 623/11 |
| 5,776,184 | 7/1998 | Tuch | 623/1 |
| 5,779,732 | 7/1998 | Amundson | 606/198 |
| 5,837,008 | 11/1998 | Berg et al. | 623/1 |

FOREIGN PATENT DOCUMENTS

| | | |
|---|---|---|
| 0 166 998 A2 | 1/1986 | (EP) . |
| 0 274 846 B1 | 7/1988 | (EP) . |
| 0 294 905 A1 | 12/1988 | (EP) . |
| 0 389 632 A1 | 10/1990 | (EP) . |
| 0 395 098 A1 | 10/1990 | (EP) . |
| 0 407 965 A1 | 1/1991 | (EP) . |
| 0 439 908 A1 | 8/1991 | (EP) . |
| 0 470 246 B1 | 2/1992 | (EP) . |
| 0 470 569 A1 | 2/1992 | (EP) . |
| 0 480 809 A2 | 4/1992 | (EP) . |
| 0 480 809 A3 | 4/1992 | (EP) . |
| 0 543 653 A1 | 5/1993 | (EP) . |
| 0 551 182 A1 | 7/1993 | (EP) . |
| 0 567 816 A1 | 11/1993 | (EP) . |
| 0 568 310 A1 | 11/1993 | (EP) . |
| 0 592 870 A1 | 4/1994 | (EP) . |
| 0 604 022 A1 | 6/1994 | (EP) . |
| 0 611 576 A1 | 8/1994 | (EP) . |
| 0 623 354 A1 | 11/1994 | (EP) . |
| 0 706 376 B1 | 4/1996 | (EP) . |
| 0832618 * | 1/1998 | (EP) . |
| 1 435 797 A1 | 10/1973 | (GB) . |
| 2 128 500 A1 | 5/1984 | (GB) . |
| WO 90/01969 A1 | 3/1990 | (WO) . |
| WO 90/13332 A1 | 11/1990 | (WO) . |
| WO 91/00163 A1 | 1/1991 | (WO) . |
| WO 91/07154 A1 | 5/1991 | (WO) . |
| WO 91/10424 A1 | 7/1991 | (WO) . |
| WO 91/11193 A1 | 8/1991 | (WO) . |
| WO 91/12779 A1 | 9/1991 | (WO) . |
| WO 92/00747 A1 | 1/1992 | (WO) . |
| WO 92/09073 A1 | 5/1992 | (WO) . |
| WO 92/12717 A2 | 8/1992 | (WO) . |
| WO 92/15286 A1 | 9/1992 | (WO) . |
| WO 93/06792 A1 | 4/1993 | (WO) . |
| WO 93/11120 | | |

| | | |
|---|---|---|
| WO 94/21308 A1 | 6/1993 | (WO) . |
| WO 95/03795 A1 | 9/1994 | (WO) . |
| WO 96/03092 A1 | 2/1995 | (WO) . |
| WO 96/03984 A1 | 2/1996 | (WO) . |
| WO 96/25176 A1 | 2/1996 | (WO) . |
| WO 96/26689 A1 | 8/1996 | (WO) . |
| WO 98/36784 A1 | 9/1996 | (WO) . |
| | A1 | 8/1998 | (WO) . |

OTHER PUBLICATIONS

Guyton, John R. et al., "Inhibition of Rat arterial Smooth Muscle Cell Prolicferation by Heparin," *Circulation Research*, vol. 46, No. 5, May 1980, pp. 625–634.

Jampel, Henry D., M.D. et al., "In Vitro Release of Hydrophobic Drugs From Polyanhydride Disks", *Ophthalmic Surgery*, dated prior to Jan. 8, 1991.

Kawahito, Koji et al., "Heparin Coated Percutaneous Cardiopulmonary Support for the Treatment of Circulatory Collapse After Cardiac Surgery," *ASAIO Journal* vol. 40, No. 4, Oct–Dec 1994, pp. 972–976.

Kishida, Akio et al., "Immobilization of Human Thrombomodulin onto Biomaterials," *ASAIO Journal , Slide Forum—Materials 4* (1994) pp. M840–M845.

Lambert, T. et al., "A New Method For Arterial Drug Delivery Removable Stent", *JACC*, vol. 21, No. 2, Abstract No. 334–2 (1993) p. 483A.

Lambert, T. et al., "Localized Arterial Drug Delivery From a Polymer Coated Removable Metallic Stent: Kinetics and Bioactivity of Forskolin", *Circulation Abstracts From the 66th Scientific Sessions*, vol. 88, No. 4, Part 2, Abstract No. 1659 (1993) p. I–3.

Linhardt, Robert J. et al., "Differential Anticoagulant Activity of Heparin Fragments Prepared Using Microbial Heparinase," *The Journal of Biological Chemistry*, vol. 257, No. 13, Jul. 10, 19xx, pp. 7310–7313.

Miyama, Hajime et al., "A New Antithrombogenic Heparinized Polymer," *J. Biomed Mater. Res.*, vol. 11 (1977) pp. 251–265.

Moses, Marsha A. et al., *Inhibitors of Angiogenesis*, Review, The Children's Hopsital Medical Center, Boston, MA, dated prior to Jan. 8, 1999.

Nichols, Allen B. et al., "Effect of Heparin Bonding on Catheter–induced Fibrin Formatioin and Platelet Activation," *Circulation*, vol. 70, No. 5, Nov. 1984, pp. 843–850.

Pitt, C.G. et al., "The Design of Controlled Drug Delivery Systems Based on Biodegredable Polymers", *Progress in Contraceptive Delivery Systems*, M T P Press, Lancaster, vol. 1 (1980) pp. 17–18.

Sheppeck, Richard A. et al., "Examination of the Roles of Glycoprotein Ib and Glycoprotein IIb/IIIa in Platelet Deposition on an Artifical Surface Using Clinical Antiplatelet Agents and Monoclonal Antibody Blockade," *Blood*, vol. 78, No. 3, Aug. 1, 1991, pp. 673–680.

Tang, Chris et al., "Regression of Collagen–Induced Arthritis with Taxol, A Microtubule Stabilizer", *Arthritis Rheum.*, vol. 36, No. 9 (Suppl.) (1993) p. 42.

"A Powerful Case For LOPID", Parke–Davis, dated prior to Jan. 8, 1999.

Whitborne, Richard, Ph.D., Presentation at the $2^{nd}$ International Coronary Stenting Summit (Mar. 1–2, 1991).

Wilson, Dr. Joseph, "Thromboresistant Plastic Coating Treatment," *Research Partners, Inc.*, Internet Article dated Jan. 21, 1991, 2 pages.

* cited by examiner

STENTS WITH HYBRID COATING FOR MEDICAL DEVICES

CROSS REFERENCES TO CO-PENDING APPLICATIONS

The present application is a continuation-in-part of U.S. patent application Ser. No. 08/929,948, filed Sep. 15, 1997, now U.S. Pat. No. 6,048,620 entitled "A Hydrophilic Coating and Substrates, Particularly Medical Devices, Provided with Such A Coating", which is a divisional of Ser. No. 08/392,141, filed Feb. 22, 1995, now U.S. Pat. No. 5,702,754, issued Dec. 30, 1997, the disclosure of which are incorporated herein by reference.

FIELD OF THE INVENTION

The present invention relates generally to implantable medical devices. More specifically, the present invention relates to vascular or cardiovascular stents having a time-release coating for inhibiting restenosis and a non-thrombogenic coating for inhibiting clot formation on the stent. In particular, the present invention includes stents having a first coating of Taxol admixed with a polymer and a second coating of heparin bonded to the first coating through a crosslinking agent.

BACKGROUND OF THE INVENTION

Vascular disease is a leading cause of death and disability in the developed world. In the United States, more than one half of all deaths are due to cardiovascular disease. Atherosclerosis is the most common form of vascular disease and leads to insufficient blood supply to body organs, which can result in hearts attacks, strokes, and kidney failure. Atherosclerosis is a form of vascular injury in which the vascular smooth muscle cells in the artery wall undergo hyperproliferation and invade and spread into the inner vessel lining, which can make the vessels susceptible to complete blockage when local blood clotting occurs. This can lead to death of the tissue served by that artery. In the case of a coronary artery, this blockage can lead to myocardial infarction and death.

Coronary artery blockage can be treated with coronary artery bypass surgery and/or angioplasty. Both procedures may initially appear to be successful, but are in effect undone by the effect of restenosis or the recurrence of stenosis after such a treatment. Restenosis is believed to include hyperproliferation of vascular smooth muscle cells. In particular, one third of patients treated using angioplasty have restenosis and blockage within 6 months after the procedure.

To prevent vessel blockage from restenosis, stents are used. Stents are nominally tubular structures and can have either solid walls or lattice like walls, and can be either expandable or self-expanding. After angioplasty balloon dilatation, the previously constricted vessel is at least temporarily widened. A stent can be delivered on a catheter and expanded in place or allowed to expand in place against the vessel walls. With the stent in place, restenosis may or may not be inhibited, but the probability and/or degree of blockage is reduced due to the structural strength of the stent opposing the inward force of any restenosis. Restenosis may occur over the length of the stent and be at least partially opposed by the stent. Restenosis may also occur past the ends of the stent, where the inward forces of the stenosis are unopposed.

Therapeutic agents to inhibit restenosis have been used with varying success. Taxol, an antimicrotubule agent isolated from the bark of the western Pacific Yew tree, is especially effective in inhibiting some cancers and is believed to be effective in combating restenosis. Systemic administration of Taxol can have undesirable side effects, making local administration a preferred mode of treatment. Local administration of Taxol may be more effective when carried out over a longer time period, such as a time period at least matching the normal reaction time of the body to the angioplasty. Local administration of Taxol over a period of days or even months may be most effective in inhibiting restenosis. Such a long time period may be provided by a time release delivery system from the stent itself.

Leaving a stent in place for long time periods in contact with the blood stream can subject the stent to thrombus formation, which can also narrow the vessel inside diameter. A stent surface used to release a therapeutic agent such as Taxol may also not inhibit thrombus formation. What would be desirable is a stent having restenosis inhibiting properties and be suitable for being left in place for long periods without acting as a site for thrombus formation.

SUMMARY OF THE INVENTION

The present invention includes a substrate such as a stent body, means for inhibiting restenosis, means for adhering the restenosis inhibiting means to the body, and means for releasing the restenosis inhibiting means over time. The present invention also includes means for rendering the body non-thrombogenic. In one stent, means for inhibiting restenosis includes paclitaxel (taxol), analogues, and/or derivatives thereof. In one stent, means for adhering the restenosis inhibiting means to the body and releasing the restenosis inhibiting means from the body over time includes admixing the restenosis inhibiting means in a polymeric material adhered to the stent body. In one stent, means for rendering the stent non-thrombogenic includes bonding a crosslinking agent to the polymeric material and then bonding a non-thrombogenic material, such as heparin, to the crosslinking agent. In one stent the polyfunctional crosslinking agent includes polyfunctional aziridine, and the polymeric material includes organic acid functional groups capable of forming covalent bonds with the polyfunctional aziridine.

The present invention includes methods for providing a substrate such as a stent with a biocompatible and restenosis inhibiting coating. One method includes coating the substrate with a first aqueous coating composition, the composition including an aqueous dispersion or emulsion of a polymer, a first therapeutic agent, and an excess of a polyfunctional crosslinking agent having functional groups capable of reacting with the polymer. The method can further include drying the first coating composition to obtain a substantially water insoluble coating or layer still including active functional groups. The method further includes forming a biocompatible surface over the first coating composition by contacting the first dried coating composition with a second aqueous coating composition including an aqueous solution or dispersion of a biocompatibility agent, and drying the combined coatings to bind the biocompatibility agent to the excess crosslinking agent. In one method the biocompatibility agent is a non-thrombogenic agent. In one method, the non-thrombogenic agent includes heparin.

In one method, the polymer includes organic acid functional groups such as carboxylic or sulfonic acid and includes a polyfunctional crosslinking agent capable of reacting with the organic acid groups. In one method, the polymer includes water borne polyurethane, the first therapeutic agent includes paclitaxel, analogues, and/or derivatives thereof, the polyfunctional crosslinking agent includes polyfunctional aziridine, and the second aqueous coating composition includes an aqueous solution or dispersion of heparin.

DETAILED DESCRIPTION OF THE INVENTION

The present invention includes a therapeutic, biocompatible coating over a substrate. One article suitable for incorporating the present invention is a stent suitable for implantation within a body vessel such as a coronary blood vessel. A preferred stent made according to the present invention includes a first, restenosis inhibiting therapeutic agent admixed in a polymeric layer which together coat the stent and a second, non-thrombogenic therapeutic agent coating the first coating.

Substrates suitable for incorporating the present invention include, for example, plastics, other polymeric materials, metals, metallic wires, glass and ceramics. A preferred apparatus incorporating the present invention is a stent, in particular a coronary artery stent formed of a metallic material such as Nitinol or stainless steel.

One stent made according to the present invention includes a polymeric layer coating the stent. Polymers having organic acid functional groups are preferred. In particular, organic acid groups such as carboxylic acid or sulfonic acid are preferred. In the present context the term "organic acid group" is meant to include any groupings which contain an organic acidic ionizable hydrogen, such as carboxylic and sulfonic acid groups. The expression "organic acid functional groups" is meant to include any groups which function in a similar manner to organic acid groups under the reaction conditions, for instance metal salts of such acid groups, particularly alkali metal salts like lithium, sodium and potassium salts, and alkaline earth metal salts like calcium or magnesium salts, and quaternary amine salts of such acid groups, particularly quaternary ammonium salts.

The polymer having organic acid functional groups, which is included in the first aqueous coating composition, is selected with due regard for the nature of the substrate to be coated. Typically the polymer in the first coating composition will be selected from homo- and co-polymers including vinylic monomer units, polyurethanes, epoxy resins, and combinations thereof. The polymer in the first coating composition is preferably selected from polyurethanes, polyacrylates, polymethacrylates, polyisocrotonates, epoxy resins, acrylate-urethane co-polymers, and combinations thereof having organic acid functional groups. In a particularly preferred embodiment of the method according to the invention, the polymer in the first coating composition is selected from homo- and co-polymers having a substantial amount of organic acid functional groups in their structure, which may act as an internal emulsifier. A specific class of polyurethanes which may be used in the first coating composition are the so-called water-borne polyurethanes, among which are the so-called internally emulsified water-borne polyurethane containing carboxylic acid groups and/or sulfonic acid groups, optionally as salts of such groups, as internal emulsifiers are particularly preferred.

Examples of water-borne polyurethanes are those supplied under the tradename NeoRez by Zeneca Resins, for instance NeoRez-940, NeoRez-972, NeoRez-976, and NeoRez-981; under the tradename Sancure by Sanncor, for instance Sancure 2026, Sancure 2710, Sancure 1601, and Sancure 899; under the tradenames U21 and U21X by B.F. Goodrich; and under the tradenames Bayhydrol LS-2033, Bayhydrol LS-2100, Bayhydrol LS-2952, and Bayhydrol LS-2990 by Bayer AG.

Another specific class of polymers which have shown to be particularly useful in the first coating composition are acrylate-urethane co-polymers, for instance the acrylic urethane co-polymer dispersions supplied under the tradenames NeoPac E-106, NeoPac E-121, NeoPac E-130, and NeoRez R-973 by Zeneca Resins.

The concentration of the polymer in the first coating composition is usually from about 2 to about 60% by weight and preferably from about 5 to about 40% by weight calculated as solids of polymer compared to the total weight of the first coating composition.

In addition to one or more polymers having organic acid functional groups, the first aqueous coating composition can comprise one or more polyfunctional crosslinking agents having functional groups being capable of reacting with organic acid groups. Polyfunctional crosslinking agents having functional groups being capable of reacting with organic acid groups are known in the art. For instance such polyfunctional crosslinking agents have been used for external crosslinking of polyurethanes.

Particularly preferred polyfunctional crosslinking agents for use in the method according to the invention are polyfunctional aziridines and polyfunctional carbodimides. Polyfunctional aziridines and polyfunctional carbodimides and their use as crosslinking agents are known in the art.

The crosslinking agent supplied by Zeneca Resins under the tradename NeoCryl CX 100 and the crosslinking agent supplied by EIT Industries under the tradename XAMA-7 are specific examples of polyfunctional aziridine crosslinking agents which may be used in the method according to the invention, and the crosslinking agent supplied by Union Carbide under the tradename Ucarlink XL-29SE is a specific example of a polyfunctional carbodimide crosslinking agent which may be used in the method according to the invention.

Among the polyfunctional aziridines useful in the present invention is the trifunctional aziridine of the following formula:

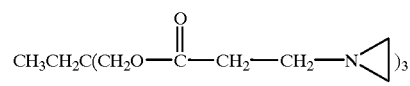

The polyfunctional crosslinking agent is preferably a crosslinking agent having more than two functional groups per molecule. Furthermore, it should be noted that a combination of polyfunctional crosslinking agents may be used in the method according to the invention.

The functional groups on the crosslinking agent can serve two purposes. The first purpose is to crosslink the first polymeric coating. The second purpose is to participate in covalent bonding with the organic acid groups present in the second coating. As such, there is preferably sufficient functionality in the crosslinking agent to accomplish both purposes. That is, the amount of crosslinking agent used preferably provides sufficient functional groups to substantially crosslink the first polymeric coating so that enough unreacted functional groups remain to covalently bond to the second layer.

One indication that insufficient functional groups from the crosslinking agent are present is the inadequate bonding of the second layer. This can be evidenced by the lack of wear resistance as such coatings can be easily wiped off the substrate to which they are applied.

The concentration of the crosslinking agent in the first coating composition is usually in the range from about 0.2 to about 30% by weight and preferably in the range from about 0.5 to about 20% by weight.

As is known in the art, the first aqueous coating composition may include other conventional additives like leveling agents, various stabilizers, pH adjustment agents, defoaming agents, cosolvents, etc., if compatible with the intended use of the coated substrate.

The coating of the first aqueous coating composition is preferably dried so as to obtain a substantially water-insoluble coating layer still including functional groups being reactive with organic acid groups. Hereafter, the obtained dried coating is contacted with a second aqueous coating composition comprising an aqueous solution or dispersion of a non-thrombogenic agent, after which the second coating is dried, the non-thrombogenic agent thereby becoming bonded to the polymer of the first coating composition through the crosslinking agent.

A first therapeutic agent is included in the first coating or layer. The first therapeutic agent is preferably a restenosis inhibiting agent. A preferred restenosis inhibiting agent includes a microtubule stabilizing agent such as paclitaxel (taxol), analogues, derivatives, and mixtures thereof. For example, derivatives believed suitable for use in the present invention include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt.

The first therapeutic agent is preferably mixed with the polymer, water, and crosslinking agent to form an aqueous dispersion or emulsion. The polymeric emulsion or dispersion can be applied to the substrate to be coated and allowed to dry. A preferred method of drying is air drying.

The second coating can be prepared by dissolving heparin in water. In a preferred embodiment, the heparin concentration is between about 0.05 weight percent and about 20 weight percent. In a more preferred embodiment, the heparin concentration is between about 0.5 and about 10 weight percent. In a most preferred embodiment, the heparin concentration is about 2 percent. In one method, the stent or article having the first dried coating is dipped in the heparin solution, taken out and allowed to air dry. The finished coating is subject to ambient temperature or elevated temperature drying in order to allow the heparin to bond to the polymer layer of the first coating composition.

Some methods according to the present invention are effective at relatively low temperatures, and particularly at ambient or room temperature, to allow for use with heat sensitive substrates, pharmacentical agents and biomolecules. In one embodiment of the method according to the invention, the functional groups of the crosslinking agent are capable of reacting with the organic acid functional groups of the polymer in the first coating composition and the organic acid functional groups of the second coating at a temperature in the range of 10° C.–70° C., preferably at a temperature in the range of 15° C.–35° C. Such reactivity of the crosslinking agent makes it possible to coat the substrate at a temperature in the range of 10° C.–70° C., for example at a temperature in the range of 15° C.–35° C., such as at room temperature, although, of course, higher drying temperatures can be used if desired.

The drying time will depend on the drying temperature, higher drying temperatures requiring shorter drying time and vice versa. However, it will be within the ordinary skill of a person skilled in the art to determine a suitable combination of drying temperatures and drying time for a specific coating. In many cases drying at about room temperature for about 12 hours will be adequate.

The preferred result is a water insoluble polymeric layer having a first therapeutic agent admixed therein and able to be released under physiological temperature and pH. The preferred result also contains the crosslinking agent bonded to the polymeric material and having a substantial number of active functional groups remaining and capable of bonding additional material to the first layer. In one embodiment, the aqueous dispersion or emulsion includes polyurethane, taxol, and polyfunctional aziridine.

A second coating or layer can be added to the first layer by preparing an aqueous solution or emulsion of a second therapeutic agent capable of being bound by the crosslinking agent. The second therapeutic agent is preferably a non-thrombogenic agent. A preferred non-thrombogenic agent includes heparin. After the application of the second therapeutic agent, the second layer is allowed to dry.

The article or stent resulting from the above disclosed process includes a first therapeutic agent admixed in a polymeric material which can be released over time under physiological temperature and pH. The article or stent also includes a second therapeutic agent covalently bound to the first layer by a crosslinking agent. The second therapeutic agent preferably has non-thrombogenic properties.

The invention will be further illustrated in the following non-limiting examples representing presently preferred embodiments of the first coating and second coating of the invention.

EXAMPLE 1

A first coating composition is prepared by adding the following ingredients successively to a glass beaker under agitation until thoroughly mixed.

| | |
|---|---|
| NeoRez R981 | 20 ml |
| N-methyl-pyrrolidone (NMP) | 10 ml |
| 50% Taxol solution in NMP (g Taxol/ml NMP) | 15 ml |
| Neocryl CX 100 | 4 ml |

NeoRez R981 (from Zeneca Resins) is a polyester-based, aliphatic water-borne polyurethane containing carboxylic acid groups as internal emulsifier, which is stabilized by triethylamine (TEA) and has a solids content of 32% and a pH of 7.5–9.0 at 25° C. It contains a 5.3% N-methyl-pyrrolidone as cosolvent. NeoCryl CX 100 (from Zeneca Resins) is a polyfunction aziridine crosslinking agent. Taxol (from Hauser) is 99.9% dissolved in NMP as stock solution

EXAMPLE 2

In the same manner as in Example 1, a first coating composition is prepared using the following ingredients:

| | |
|---|---|
| Bayhydrol 121 | 20 ml |
| NMP | 20 ml |
| 50% Taxol solution in NMP (g Taxol/ml NMP) | 25 ml |
| Neocryl CX 100 | 2 ml |
| Ethanol | 10 ml |

Bayhydrol 121 is an anionic dispersion of an aliphatic polycarbonate urethane polymer in water/n-methyl-2-pyrrolidone. It has a solid content of 35%, and a pH of 7.5–9.0. It contains 15% of n-methyl-2-pyrrolidone. Ethanol is used to adjust the viscosity of the fluid.

EXAMPLE 3

A first coating composition is prepared as described in Example 1, using the following ingredients:

| | |
|---|---|
| Bayhydrol 121 | 20 ml |
| NMP | 20 ml |
| 50% Taxol solution in NMP (g Taxol/ml NMP) | 25 ml |
| Ucarlink XL-29SE | 2 ml |
| Ethanol | 10 ml |

Ucarlink XL-29SE is a polyfunctional carbodiimide, available from Union Carbide.

EXAMPLE 4

A second coating composition is prepared by adding the following ingredients successively to a glass beaker under agitation until thoroughly mixed.

| | |
|---|---|
| Heparin (from Abbott) | 2 g |
| De-ionized water | 20 ml |
| 34% ammonium hydroxide | 0.1 ml |

EXAMPLE 5

In the same manner as Example 4, a second coating composition is prepared using the following ingredients:

| | |
|---|---|
| Hyaluronic acid (sodium salt) | 2 g |
| De-ionized water | 20 ml |
| 34% ammonium hydroxide | 0.1 ml |

EXAMPLE 6

In the same manner as Example 4, a second coating is prepared using the following ingredients:

| | |
|---|---|
| Heparin | 2 g |
| Hyaluronic acid (sodium salt) | 1 g |
| De-ionized water | 20 ml |
| 34% ammonium hydroxide | 0.1 ml |

EXAMPLE 7

A stainless steel stent is cleaned by immersion in isopropanol under ultrasound, then dried. The first coating composition from Example 1 is applied to the stent surface by spraying, and the coating air dried for 10 minutes at ambient temperature. The second coating composition from Example 3 is applied to the stent by spraying, and allowed to air dry at ambient temperature for 10 minutes. The coated stent is then placed in a 50° C. oven overnight.

EXAMPLE 8

A Nitinol self-expanded stent is cleaned in the same manner as in Example 7. The first coating composition from Example 2 is applied to the stent by dipping the stent into the coating solution. The coating is air dried for 5 minutes. The dipping process is repeated 10 times in order to build a thick coating layer on the stent. After the last dip of the first coating composition, the stent is allowed to air dry for 5 minutes, then the second coating composition is applied by dipping. The process is repeated once, then the stent is air dried for 10 minutes. The finish coating is cured under 37° C. for 48 hours.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A stent comprising:
    a substantially tubular body;
    a first coating disposed over said body, said first coating including a polymeric material, a first therapeutic agent admixed in said polymeric material, and a crosslinking agent; and
    a second coating disposed over said first coating including a second therapeutic agent, wherein said crosslinking agent binds said second therapeutic agent to said polymeric material.

2. A stent as recited in claim 1, wherein said second therapeutic agent has non-thrombogenic properties.

3. A stent as recited in claim 1, wherein said second therapeutic agent is covalently bound to said crosslinking agent.

4. A stent as recited in claim 1, said first therapeutic is selected from the group consisting of paclitaxel, paclitaxel analogues, paclitaxel derivatives, and combinations thereof, and said second therapeutic agent includes heparin.

5. A stent as recited in claim 1, wherein said crosslinking agent includes polyfunctional aziridine.

6. A stent comprising:
    a substantially tubular body;
    means for inhibiting restenosis;
    means for adhering said restenosis inhibiting means to said stent body and releasing said restenosis inhibiting means from said stent body over time; and
    means for rendering said stent body non-thrombogenic.

7. A stent comprising:
    a substantially tubular body;
    a polymer having organic acid functional groups;
    a first coating layer including a first therapeutic agent admixed with said polymer and a polyfunctional crosslinking agent covalently bonded to said polymer organic acid functional groups; and
    a second coating layer disposed over said first coating layer including a second therapeutic agent covalently bonded to said polyfunctional crosslinking agent.

8. A stent as recited in claim 7, wherein said first therapeutic agent is capable of diffusing out of said first layer.

9. A stent as recited in claim 7, wherein said second therapeutic agent is biocompatible with a human blood stream.

10. A stent as recited in claim 7, wherein said first therapeutic agent includes taxol, analogues, or derivatives thereof and said second therapeutic agent has non-thrombogenic properties.

11. A stent as recited in claim 7, wherein said first therapeutic agent includes pacitaxel, analogues, or derivatives thereof, said polymer includes polyurethane, said crosslinking agent includes a polyfunctional aziridine, and said second therapeutic agent includes heparin, wherein said polyfunctional aziridine is covalently bonded to said polyurethane and to said heparin.

12. A method for providing a substrate with a biocompatible and restenosis inhibiting coating comprising the steps of:

coating said substrate with a first aqueous coating composition including a polymer having organic acid functional groups, a first therapeutic agent, an excess of a polyfunctional crosslinking agent having functional groups capable of reacting with organic acid groups;

drying said first coating composition to obtain a substantially water insoluble coating layer still including functional groups being reactive with organic acid groups;

forming a non-thrombogenic surface over said first coating composition by contacting said dried first coating composition with a second aqueous coating composition including heparin; and drying said second coating, to bond said heparin to said excess crosslinking agent.

13. A method according to claim 12, wherein said organic acid functional groups are selected from the group consisting of free carboxylic and sulfonic acid groups, metal salts of said acid groups, alkali metal salts of said acid groups, and quaternary amine salts of said acid groups.

14. A method according to claim 12, wherein said polyfunctional crosslinking agent is selected from polyfunctional aziridines, polyfunctional carboimides, and combinations thereof.

15. A method according to claim 12, wherein said polymer in said first coating composition is selected from the group consisting of polyurethanes, polyacrylates, polymethacrylates, polyisocrotonates, epoxy resins, acrylate-urethane co-polymers, and combinations thereof.

16. A method according to claim 15, wherein said polymer in the first coating composition selected from the group consisting of acrylate-urethane co-polymers, polyurethane, and mixtures thereof.

* * * * *

UNITED STATES PATENT AND TRADEMARK OFFICE
CERTIFICATE OF CORRECTION

PATENT NO.   : 6,231,600 B1
DATED        : May 15, 2001
INVENTOR(S)  : Sheng-Ping Zhong It is certified that error appears in the above-identified patent and that said Letters Patent is hereby corrected as shown below:

<u>Title page,</u>
Item [75], Inventor: "Sheng-ping Zhong" should read -- Sheng-Ping Zhong --.

Signed and Sealed this

Second Day of July, 2002

Attest:

Attesting Officer

JAMES E. ROGAN
*Director of the United States Patent and Trademark Office*